(12) United States Patent
Matsumoto et al.

(10) Patent No.: US 8,133,677 B2
(45) Date of Patent: Mar. 13, 2012

(54) **METHOD FOR MEASURING THE NUMBER OF ORAL *LACTOBACILLUS*, AND A PCR PRIMERS-PROBE SET USED FOR THE SAME**

(75) Inventors: Yuko Matsumoto, Tokyo (JP); Yoko Ishihara, Tokyo (JP)

(73) Assignee: GC Corporation, Tokyo (JP)

( * ) Notice: Subject to any disclaimer, the term of this patent is extended or adjusted under 35 U.S.C. 154(b) by 176 days.

(21) Appl. No.: 12/057,789

(22) Filed: Mar. 28, 2008

(65) Prior Publication Data

US 2009/0111103 A1  Apr. 30, 2009

(30) Foreign Application Priority Data

Mar. 30, 2007 (JP) ................ 2007-090279

(51) Int. Cl.
*C12Q 1/68* (2006.01)
*C12P 19/34* (2006.01)
*C07H 21/04* (2006.01)
(52) U.S. Cl. .............. 435/6.12; 435/91.2; 536/24.33
(58) Field of Classification Search .............. None
See application file for complete search history.

(56) References Cited

U.S. PATENT DOCUMENTS 5,705,339 A  1/1998  Nietupski et al.

FOREIGN PATENT DOCUMENTS

| JP | 10210980 | 8/1998 |
| JP | 2004329161 | 11/2004 |
| JP | 2005006556 | 1/2005 |
| WO | 2005/033337 | 4/2005 |

OTHER PUBLICATIONS

Lowe et al. Nucleic Acids Research vol. 18:1757-1761. 1990.*
Galaviz et al., "Caries risk in children: determined by levels of mutans streptocci and *Lactobaccilus*", The Journal of Clinical Pediatric Dentistry, vol. 29(4), 2005, 329-334.
Crossner, "Salivary *Lactobacillus* counts in the prediction of caries activity", Community Dentistry and Oral Epidemiology, Denmark, 1981, vol. 9, 182-190.
Nishikawara et al., "Correlation of cariogenic bacteria and dental caries in adults", Journal of Oral Science, vol. 48 (4), 2006, 245-251.
Byun et al., "Quantitative Analysis of Diverse *Lactobacillus* Species Present in Advanced Dental Caries", Journal of Clinical Microbiology, Jul. 2004, vol. 42(7), 3128-3136.
Martin et al., "Quantitative Microbiological Study of Human Carious Dentine by Culture and Real-Time PCR: Association of Anaerobes with Histopathological Changes in Chronic Pulpitis", Journal of Clinical Microbiology, vol. 40 (5), May 2002, 1698-1704.
European Search Report for corresponding European Patent Application No. EP08103048.

* cited by examiner

*Primary Examiner* — Kenneth R. Horlick
(74) *Attorney, Agent, or Firm* — Heslin Rothenberg Farley & Mesiti P.C.

(57) ABSTRACT

There is provided a real-time PCR assay capable of measuring the number of *lactobacillus* present in an oral cavity, in a short time. The object can be solved by a method for measuring the number of oral *lactobacillus* using a combination of a forward primer comprising a oligonucleotide part of at least 15 sequential bases in the base sequence any one of SEQ ID NO: 1 to 4 and a reverse primer comprising a oligonucleotide part of at least 15 sequential bases in the base sequence any one of SEQ ID NO: 5 to 7; and a probe for measuring the number of oral *lactobacillus*, comprising a oligonucleotide part of at least 10 sequential bases in the base sequence any one of SEQ ID NO: 8 to 15.

7 Claims, No Drawings

METHOD FOR MEASURING THE NUMBER OF ORAL *LACTOBACILLUS*, AND A PCR PRIMERS-PROBE SET USED FOR THE SAME

CROSS-REFERENCE TO RELATED APPLICATIONS

This application claims the priority of Japanese Patent Application No. 2007-090279 filed on Mar. 30, 2007.

TECHNICAL FIELD

The present invention relates to a method for measuring the number of oral *lactobacillus*, and a PCR primers-probe set used for the same.

BACKGROUND ART

It is known that the presence of mutans streptococci in the oral cavity of a human is closely associated with a development of dental caries. Mutans streptococci can attach to a surface of a tooth via insoluble glucan produced by mutans streptococci, and can grow by metabolizing sucrose to produce lactic acid in an acid environment. *Lactobacillus*, which can produce lactic acid and grow under a condition of an acid environment, is also considered a bacterial cause of dental caries, although *Lactobacillus* do not have an ability to attach to a surface of a tooth (non-patent reference 1, non-patent reference 2, and non-patent reference 3).

In a report of the non-patent references 1 to 3, the number of *lactobacillus* was measured by means of the culture method. It was demonstrated that a patient with high numbers of *lactobacillus* determined by the culture method has at high risk of a development of dental caries. Therefore, measurement of the number of *lactobacillus* is important for a prediction of the risk of development of dental caries. However, the conventional culture method takes two or more days to obtain a measurement result, and a procedure of the culture method is carried out by hand.

As a measuring method of the number of *lactobacillus* other than the culture method, a real-time PCR assay has been developed by designing primers having base sequences common among all kinds of *lactobacillus*, to thereby measure the number of *lactobacillus* in saliva or bacterial plaque, in a short time (non-patent reference 4). These primers are designed on the basis of common base sequence region in the 16S ribosomal RNA gene of genus *Lactobacillus*, including nine *Lactobacillus* species. However, the primers include a base sequences part which exhibits high homology to base sequences of oral bacteria other than *lactobacillus*, and so, it is considered that specificity of the primers is low. Further, it is not clear whether or not the number of *lactobacillus* obtained by the reported real-time PCR assay is correlated to that obtained by the culture method.

Therefore, the culture method is most appropriate for a predicting accurately the risk of development of dental caries by measuring the number of *lactobacillus* in an oral cavity. However, the culture method is very time-consuming, and thus is not efficient. Therefore, the culture method requires considerable labor when many samples are tested in, for example, a medical laboratory.

[Non-Patent Reference No. 1] The Journal of Clinical Pediatric Dentistry, U.S.A, 2005, vol. 29, p. 329-33

[Non-Patent Reference No. 2] Community Dentistry and Oral Epidemiology, Denmark, 1981, vol. 9, p. 182-90

[Non-Patent Reference No. 3] Journal of Oral Science, Japan, 2006, vol. 48, p. 245-51

[Non-Patent Reference No. 4] Journal of Clinical Microbiology, U.S.A, 2004, vol. 42, p. 3128-36

DISCLOSURE OF THE INVENTION

Problems to be Solved by the Invention

The present inventors tried measuring the number of oral *lactobacillus* by the real-time PCR assay using the primers described in non-patent reference No. 4. However, obtained results were not correlated with those obtained by the culture method. Under these circumstances, the present inventors conducted intensive studies into a method for, in a short time, accurately measuring the number of oral *lactobacillus* by real-time PCR assay. As a result, the inventors focused their attention on the base sequence of 16S ribosomal RNA included in the 30S subunit of prokaryotic ribosome, and designed primers, and primers and probes for use in real-time PCR assay by selecting regions of base sequences commonly present in all oral *lactobacillus*. Then, the inventors carried out real-time PCR assays using the primers, and the primers and probes, and found the specific primers and probes for measuring the number of oral *lactobacillus* present in an oral cavity. The number of oral *lactobacillus* obtained by the real-time PCR assay using the specific primers and probes accurately correlates with those obtained by the culture method.

The present invention is based on the above findings.

Means for Solving the Problems

The present invention relates to a primer set for measuring the number of oral *lactobacillus*, comprising at least one forward primer comprising an oligonucleotide part of at least 15 sequential bases in a base sequence of 5'-GCCGTAAAC-GATGARTGCTARGTGTTGGRRGGTTTC-3' (wherein R is A or G; SEQ ID NO:1), 5'-GCCGTAAACGATGAAT-GCTAGGTGTTGGAGGGTTTC-3' (SEQ ID NO:2), 5'-GC-CGTAAACGATGAGTGCTAAGTGTTGGGAGGTTTC-3' (SEQ ID NO:3), or 5'-GCCGTAAACGATGAGTGCTAG-GTGTTGGAGGGTTTC-3' (SEQ ID NO:4), and at least one reverse primer comprising an oligonucleotide part of at least 15 sequential bases in a base sequence of 5'-TGCGGTCG-TACTCCCCAGGCGGARTGCTTA-3' (wherein R is A or G; SEQ ID NO:5), 5'-TGCGGTCGTACTCCCCAGGCG-GAATGCTTA-3' (SEQ ID NO:6) or 5'-TGCGGTCG-TACTCCCCAGGCGGAGTGCTTA-3' (SEQ ID NO:7).

According to the preferable embodiment of the primer set of the present invention, the forward primer is an oligonucleotide of the base sequence of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, or a mixture of two or more of the oligonucleotides, and the reverse primer is an oligonucleotide of the base sequence of SEQ ID NO:26, SEQ ID NO:27, or SEQ ID NO:28, or a mixture of two or more of the oligonucleotides.

Further, the present invention relates to a primers-probe set comprising the primer set described above, and at least one probe comprising an oligonucleotide part of at least 10 sequential bases in a base sequence of 5'-GGTTTCCGC-CYYTCAGTGCYGSAGCTAACGCA-3' (wherein Y is T or C, and S is G or C; SEQ ID NO:8), 5'-GGTTTCCGCCCT-TCAGTGCCGCAGCTAACGCA-3' (SEQ ID NO:9), 5'-GGTTTCCGCCTCTCAGTGCTGCAGCTAACGCA-3' (SEQ ID NO:10), 5'-GGTTTCCGCCCTTCAGTGCCG-GAGCTAACGCA-3' (SEQ ID NO:11), 5'-TGCGT-TAGCTSCRGCACTGARRGGCGGAAACC-3' (wherein R is G or A, and S is G or C; SEQ ID NO:12), 5'-TGCGT-TAGCTGCGGCACTGAAGGGCGGAAACC-3' (SEQ ID NO:13), 5'-TGCGTTAGCTGCAGCACTGAGAGGCG-GAAACC-3' (SEQ ID NO:14), or 5'-TGCGTTAGCTCCG-GCACTGAAGGGCGGAAACC-3' (SEQ ID NO:15).

According to the preferable embodiment of the primers-probe set of the present invention, the probe is an oligonucleotide of the base sequence of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, or SEQ ID NO: 38, or a mixture of two or more of the oligonucleotides.

BACKGROUND INFORMATION

The present invention relates to a method for measuring the number of oral *lactobacillus* by a real-time PCR assay using the primer set described above, or a method for measuring the number of oral *lactobacillus* by a real-time PCR assay using the primers-probe set described above.

Further, the present invention relates to a real-time PCR kit for measuring the number of oral *lactobacillus*, comprising the primer set described above, or a real-time PCR kit for measuring the number of oral *lactobacillus*, comprising the primers-probe set described above.

The term measurement or measuring as used herein means quantity or quantifying. However, the oral *lactobacillus* are detected by quantifying the oral *lactobacillus*. Therefore, it is not excluded that the primer-probe sets, and the method for measuring the number of oral *lactobacillus* of the present invention are used in qualitative detection of *lactobacillus*.

EFFECTS OF THE PRESENT INVENTION

The present invention allows the number of oral *lactobacillus* to be measured accurately in a short time. The risk of development of dental caries in a patient having a high numbers of oral *lactobacillus* in an oral cavity can be effectively evaluated by measuring the number of *lactobacillus*. Further, many samples can be measured, compared with the culture method, and thus the measuring method of the present invention can be carried out effectively in a medical laboratory.

BEST MODE FOR CARRYING OUT THE INVENTION

The primer set, and the primers-probe set can be used for quantifying the number of oral *lactobacillus*. The base sequence of primers and probes in the primer set or the primers-probe set are based on the base sequence of the 16S ribosomal RNA gene, which is included in the 30S ribosome subunit of *lactobacillus*.

The term oral *lactobacillus* as used herein means all kinds of *lactobacillus* which may be present in an oral cavity. The oral *lactobacillus* includes, for example, *Lactobacillus casei, Lactobacillus salivarius, Lactobacillus rhamnosus, Lactobacillus gasseri, Lactobacillus acidophilus, Lactobacillus crispatus*, and *Lactobacillus fermentum*, but is not limited to the above *Lactobacillus* species.

The present inventors selected the base sequence regions with high homology in the 16S ribosomal RNA gene of *Lactobacillus casei, Lactobacillus salivarius, Lactobacillus rhamnosus, Lactobacillus gaseri, Lactobacillus acidophilus, Lactobacillus crispatus*, and *Lactobacillus fermentum*, and then designed some primers and probes.

However, merely selecting primers and probes having base sequence regions with high homology in all oral *lactobacillus*, without careful study, resulted in a measurement value obtained by PCR not correlated with that obtained by the culture method. Therefore, the present inventors selected the most appropriate region's base sequence for the measurement of *lactobacillus* to be designed as the primer set, and the primers-probe set, whereby developing the measuring method capable of obtaining the measurement value correlated with the number of oral *lactobacillus* obtained by the culture method.

The primer in the primer set of the present invention comprises a oligonucleotide part of at least 15 sequential bases in the base sequence of SEQ ID NO: 1, SEQ ID NO: 2, SEQ ID NO: 3, SEQ ID NO: 4, SEQ ID NO: 5, SEQ ID NO: 6, and SEQ ID NO: 7 (hereinafter referred to as a primer oligonucleotide part 1, a primer oligonucleotide part 2, a primer oligonucleotide part 3, a primer oligonucleotide part 4, a primer oligonucleotide part 5, a primer oligonucleotide part 6, and a primer oligonucleotide part 7, respectively). The primer comprising the primer oligonucleotide part 1, the primer oligonucleotide part 2, the primer oligonucleotide part 3, or the primer oligonucleotide part 4, is sometimes referred to as a region 1 primer. The primer comprising the primer oligonucleotide part 5, the primer oligonucleotide part 6, or the primer oligonucleotide part 7, is sometimes referred to as a region 2 primer. The length of each primer oligonucleotide part is preferably 15-mer or more, more preferably 16-mer or more, most preferably 18-mer or more.

The probe in the primers-probe set of the present invention comprises a oligonucleotide part of at least 10 sequential bases in the base sequence of SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15 (hereinafter referred to as a probe oligonucleotide part 8, a probe oligonucleotide part 9, a probe oligonucleotide part 10, a probe oligonucleotide part 11, a probe oligonucleotide part 12, a probe oligonucleotide part 13, a probe oligonucleotide part 14, and a probe olignucleotide part 15, respectively). The probe comprising a probe oligonucleotide part 8, a probe oligonucleotide part 9, a probe oligonucleotide part 10, and a probe oligonucleotide part 11, is sometimes referred to as a region 3 probe. The probe comprising a probe oligonucleotide part 12, a probe oligonucleotide part 13, a probe oligonucleotide part 14, and a probe oligonucleotide part 15, is sometimes referred to as a region 4 probe. The length of each probe oligonucleotide parts is preferably 10-mer or more, more preferably 12-mer or more, most preferably 14-mer or more.

Further, as the primer in the primer set of the present invention, a primer comprising a oligonucleotide part of at least 15 sequential bases in the base sequence of SEQ ID NO:8, SEQ ID NO:9, SEQ ID NO:10, SEQ ID NO:11, SEQ ID NO:12, SEQ ID NO:13, SEQ ID NO:14, or SEQ ID NO:15 (hereinafter referred to as a primer oligonucleotide part 8, a primer oligonucleotide part 9, a primer oligonucleotide part 10, a primer oligonucleotide part 11, a primer oligonucleotide part 12, a primer oligonucleotide part 13, a primer oligonucleotide part 14, and a primer oligonucleotide part 15, respectively) can be used. The primer comprising the primer oligonucleotide part 8, the primer oligonucleotide part 9, the primer oligonucleotide part 10, or the primer oligonucleotide part 11, is sometimes referred to as a region 3 primer. The primer comprising the primer oligonucleotide part 12, the primer oligonucleotide part 13, the primer oligonucleotide part 14, or the primer oligonucleotide part 15, is sometimes referred to as a region 4 primer.

The base sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 15, are shown as follows.

```
SEQ ID NO: 1 (Region 1):
5'-GCCGTAAACGATGARTGCTARGTGTTGGRRGGTTTC-3'

(wherein R is A or G.)

SEQ ID NO: 2 (Region 1):
5'-GCCGTAAACGATGAATGCTAGGTGTTGGAGGGTTTC-3'

SEQ ID NO: 3 (Region 1):
5'-GCCGTAAACGATGAGTGCTAAGTGTTGGGAGGTTTC-3'

SEQ ID NO: 4 (Region 1):
5'-GCCGTAAACGATGAGTGCTAGGTGTTGGAGGGTTTC-3'

SEQ ID NO: 5 (Region 2):
5'-TGCGGTCGTACTCCCCAGGCGGARTGCTTA-3' (wherein R is

A or G.)

SEQ ID NO: 6 (Region 2):
5'-TGCGGTCGTACTCCCCAGGCGGAATGCTTA-3'

SEQ ID NO: 7 (Region 2):
5'-TGCGGTCGTACTCCCCAGGCGGAGTGCTTA-3'

SEQ ID NO: 8 (Region 3):
5'-GGTTTCCGCCYYTCAGTGCYGSAGCTAACGCA-3' (wherein Y is T or C, and S is G or C.)

SEQ ID NO: 9 (Region 3):
5'-GGTTTCCGCCCTTCAGTGCCGCAGCTAACGCA-3'

SEQ ID NO: 10 (Region 3):
5'-GGTTTCCGCCTCTCAGTGCTGCAGCTAACGCA-3'

SEQ ID NO: 11 (Region 3)
5'-GGTTTCCGCCCTTCAGTGCCGGAGCTAACGCA-3'

SEQ ID NO: 12 (Region 4):
5'-TGCGTTAGCTSCRGCACTGARRGGCGGAAACC-3' (wherein R is G or A, and S is G or C)

SEQ ID NO: 13 (Region 4):
5'-TGCGTTAGCTGCGGCACTGAAGGGCGGAAACC-3'

SEQ ID NO: 14 (Region 4):
5'-TGCGTTAGCTGCAGCACTGAGAGGCGGAAACC-3'

SEQ ID NO: 15 (Region 4)
5'-TGCGTTAGCTCCGGCACTGAAGGGCGGAAACC-3'
```

The base sequence represented by SEQ ID NO: 47 is that of a single strand DNA of a double strand DNA of a 16S ribosomal RNA gene of *Lactobacillus rhamnosus*, which is one of the *Lactobacillus* species present in an oral cavity (GeneBank Accession No. AY675254).

The base sequence represented by SEQ ID NO: 2 corresponds to the 827th to 862th bases region in the base sequence of SEQ ID NO: 47, and *Lactobacillus casei* and *Lactobacillus salivarius* have the same base sequences. The base sequence represented by SEQ ID NO: 3 is a base sequence of the corresponding region of *Lactobacillus gasseri, Lactobacillus acidophilus*, or *Lactobacillus crispatus*, and the base sequence represented by SEQ ID NO: 4 is a base sequence of the corresponding region of *Lactobacillus fermentum*. Further, the base sequence represented by SEQ ID NO: 1 is a consensus base sequence thereof.

The base sequence represented by SEQ ID NO: 6 corresponds to the complementary base sequence of the 890th to the 919th bases region in the base sequence of SEQ ID NO: 47, and *Lactobacillus casei* and *Lactobacillus salivarius* have the same base sequences. The base sequence represented by SEQ ID NO: 7 is a base sequence of the corresponding region of *Lactobacillus gasseri, Lactobacillus acidophilus, Lactobacillus crispatus*, or *Lactobacillus fermentum*. Further, the base sequence represented by SEQ ID NO: 5 is a consensus base sequence thereof.

The base sequence represented by SEQ ID NO: 9 corresponds to the base sequence of the 857th to 888th bases region in the base sequence of SEQ ID NO: 47, and *Lactobacillus casei* and *Lactobacillus salivarius* have the same base sequences. The base sequence represented by SEQ ID NO: 10 is a base sequence of the corresponding region of *Lactobacillus gasseri, Lactobacillus acidophilus*, or *Lactobacillus crispatus*, and the base sequence represented by SEQ ID NO: 11 is a base sequence of the corresponding region of *Lactobacillus fermentum*. Further, the base sequence represented by SEQ ID NO: 8 is a consensus base sequence thereof.

The base sequence represented by SEQ ID NO: 13 corresponds to the complementary base sequence of the 857th to 888th bases region in the base sequence of SEQ ID NO: 47, and *Lactobacillus casei* and *Lactobacillus salivarius* have the same base sequences. The base sequence represented by SEQ ID NO: 14 is a base sequence of the corresponding region of *Lactobacillus gasseri, Lactobacillus acidophilus*, or *Lactobacillus crispatus*, and the base sequence represented by SEQ ID NO: 15 is a base sequence of the corresponding region of *Lactobacillus fermentum*. Further, the base sequence represented by SEQ ID NO: 12 is a consensus base sequence thereof.

The region 1 primer, the region 2 primer, the region 3 primer, and the region 4 primer, and the region 3 probe and the region 4 probe are selected from the nucleotide sequence of the 16S ribosomal RNA gene, whereby the measuring method capable of exactly measuring the number of oral *lactobacillus* present in an oral cavity is developed.

The primer may be an oligonucleotide consisting of at least 15 sequential bases in the base sequence any one of SEQ ID NO:1 to 15, preferably an oligonucleotide consisting of at least 15 sequential bases in the base sequence of SEQ ID NO: 2, or SEQ ID NO: 6, more preferably an oligonucleotide consisting of at least 15 sequential bases in 8th to 36th bases of the base sequence of SEQ ID NO: 2, or in 9th to 28th bases of the base sequence of SEQ ID NO:6. More particularly, the primer may be an oligonucleotide consisting of the base sequence any one of SEQ ID NO: 16 to 25 or any one of SEQ ID NO: 26 to 28. The primers of SEQ ID NO: 16 to 28 are shown in Table 1 and 2.

TABLE 1

| Primer | SEQ ID | Base Sequence |
|---|---|---|
| F1 | SEQ ID 16 | 5'-ACGATGAATGCTAGGTGTTGGAG-3' |
| F2 | SEQ ID 17 | 5'-ACGATGAATGCTAGGTGTTGGA-3' |
| F3 | SEQ ID 18 | 5'-CGATGAATGCTAGGTGTTGGAG-3' |
| F4 | SEQ ID 19 | 5'-ATGAATGCTAGGTGTTGGAGGGT-3' |
| F5 | SEQ ID 20 | 5'-ATGAATGCTAGGTGTTGGAGGG-3' |
| F6 | SEQ ID 21 | 5'-TGAATGCTAGGTGTTGGAGGGT-3' |

TABLE 1-continued

| Primer | SEQ ID | Base Sequence |
|---|---|---|
| F7 | SEQ ID 22 | 5'-TGAATGCTAGGTGTTGGAGGG-3' |
| F8 | SEQ ID 23 | 5'-GAATGCTAGGTGTTGGAGGGTTT-3' |
| F9 | SEQ ID 24 | 5'-AATGCTAGGTGTTGGAGGGTTTC-3' |
| F10 | SEQ ID 25 | 5'-ATGCTAGGTGTTGGAGGGTTTC-3' |

TABLE 2

| Primer | SEQ ID | Base Sequence |
|---|---|---|
| R1 | SEQ ID 26 | 5'-TACTCCCCAGGCGGAATG-3' |
| R2 | SEQ ID 27 | 5'-ACTCCCCAGGCGGAATG-3' |
| R3 | SEQ ID 28 | 5'-CCCCAGGCGGAATGCT-3' |

However, the primer in the present invention is not limited to the above primers, so long as the number of oral *lactobacillus* can be accurately measured by means of the primers. The primer may comprise the primer oligonucleotide part of at least 15 sequential bases in the base sequence any one of SEQ ID NO: 1 to 15. In the primer comprising the primer oligonucleotide part, the primer may contain nucleotides in base sequences of a 16S ribosomal RNA gene other than the base sequence of the SEQ ID NO: 1 to 15, or other nucleotides consisting of an artificial base sequence. For example, 1 to 10 nucleotides, such as a base sequence of restriction enzyme site or base sequence of tag sequence, can be added to a 5'-terminus of the above mentioned oligonucleotide. Further, a primer having an oligonucleotide in which one to several nucleotides are substituted or less than 10% of nucleotides are mismatched in the above mentioned oligonucleotide, can be used.

A length of the primer is not particularly limited, but is preferably 15-mer to 36-mer. Further, a length of the region 1 primer is not particularly limited, but is preferably 15-mer to 36-mer, more preferably 20-mer to 29-mer, most preferably 21-mer to 23-mer. Furthermore, a length of the region 2 primer is not particularly limited, but is preferably 15-mer to 30-mer, more preferably 16-mer to 25-mer, most preferably 16-mer to 20-mer.

The primer set of the present invention comprises a forward primer and a reverse primer. As the forward primer in the primer set, a primer or a combination of two or more primers can be used. Further, as the reverse primer in the primer set, a primer or a combination of two or more primers can be used.

A primers-probe set of the present invention, comprises the primer set and at least one probe, and more specifically, at least one region 1 primer (as a forward primer), at least one region 2 primer (as a reverse primer) and at least one probe. As the probe in the primers-probe set, a probe or a combination of two or more probes can be used. Further, as the forward primer in the primers-probe set, a primer or a combination of two or more primers can be used. Furthermore, as the reverse primer in the primers-probe set, a primer or a combination of two or more primers can be used.

The probe is an oligonucleotide for detecting genomic DNA, cDNA or the like by means of the method using a hybridization technique, preferably for use in real-time PCR assay, the TaqMan method. The probe can be designed from the base sequence region between the region 1 primer and the region 2 primer in the base sequence of SEQ ID NO: 47. As the probe, a nucleotide may be hybridized to the nucleotide consisting of the base sequence of SEQ ID NO: 47 or a nucleotide may be hybridized to the complementary nucleotide thereof, or a mixture of these nucleotides used. The probe which may hybridize to the nucleotide consisting of the base sequence of SEQ ID NO: 47 is preferably the region 3 probe, and/or the region 4 probe.

The probe is preferably an oligonucleotide of at least 10 sequential bases in the base sequence any one of SEQ ID No: 8 to 15, more preferably an oligonucleotide of a base sequence of any one of SEQ ID NO: 29 to 38.

TABLE 3

| Probe | SEQ ID | Base Sequence |
|---|---|---|
| P1 | SEQ ID 29 | 5'-CGCCCTTCAGTGCCGCAGCTAAC-3' |
| P2 | SEQ ID 30 | 5'-CGCCCTTCAGTGCCGCAGCTAA-3' |
| P3 | SEQ ID 31 | 5'-CGCCCTTCAGTGCCGCAGCTA-3' |
| P4 | SEQ ID 32 | 5'-CCCTTCAGTGCCGCAGCTAACGC-3' |
| P5 | SEQ ID 33 | 5'-CCTTCAGTGCCGCAGCTAACGCA-3' |
| P6 | SEQ ID 34 | 5'-GTTAGCTGCGGCACTGAAGGGCG-3' |
| P7 | SEQ ID 35 | 5'-TTAGCTGCGGCACTGAAGGGCG-3' |
| P8 | SEQ ID 36 | 5'-TAGCTGCGGCACTGAAGGGCG-3' |
| P9 | SEQ ID 37 | 5'-GCGTTAGCTGCGGCACTGAAGGG-3' |
| P10 | SEQ ID 38 | 5'-TGCGTTAGCTGCGGCACTGAAGG-3' |

The probe in the present invention is not limited to the above probes, so long as the number of oral *lactobacillus* can be accurately measured by means of the probes. Therefore, a probe having an oligonucleotide in which one to several nucleotides are substituted or less than 10% of nucleotides are mismatched in the above mentioned oligonucleotide, can be used as a probe. The term hybridize as used herein is the same as the term hybridize used under conventional conditions of a real-time PCR assay.

The probe used in a TaqMan assay is labeled by a reporter dye and a quencher dye. A labeled oligonucleotide, wherein a reporter dye is bound to one terminus such as a 5'-terminus thereof and a quencher dye is bound to the other terminus such as a 3'-terminus thereof, may be used as a probe. A conventional dye used in a PCR assay may be used as a dye without limitation. There may be mentioned 6-carboxy-fluorescein (FAM), tetrachloro-6-carboxyfluorescein (TET), 2,7-dimethoxy-4,5-dichloro-6-carboxyfluorescein (JOE), hexochloro-6-carboxyfluorescein (HEX) or the like, as a reporter dye. There may be mentioned, for example, 6-carboxy-tetramethyl-rhodamine (TAMRA), black hole quencher (BHQ) without native fluorescence or the like, as a quencher dye.

The length of the probe is not particularly limited, but is preferably 18-mer to 35-mer, more preferably 18-mer to 30-mer, most preferably 21-mer to 25-mer.

In the method for measuring the number of oral *lactobacillus* of the present invention, a polymerase chain reaction (PCR) may be used, and particularly, a real-time PCR assay may be preferably used. As the real-time PCR assay, there may be mentioned an intercalator-based real-time PCR assay wherein an intercalator which can generate fluorescence by binding to double stranded DNA, such as SYBR Green I and the primer set, are added to a PCR reaction, and a TaqMan assay wherein the probe which is labeled with reporter dye of a 5'-terminus and a quencher dye of a 3'-terminus (hereinafter referred to as a TaqMan probe) and the primer set, are added to a PCR reaction. The real-time PCR assay per se is well-known, and kits and devices therefor are commercially available. Therefore, the real-time PCR assay can be easily carried out by only synthesizing the primer set, or the primers-probe set.

When the method for measuring the number of oral *lactobacillus* is carried out by an intercalator-based real-time PCR assay, a primer set of a combination of the region 1 primer and the region 2 primer, the region 1 primer and the region 4 primer, or the region 3 primer and the region 2 primer, can be used. A primer set of a combination of the region 1 primer and the region 2 primer is preferable. When the method for measuring the number of oral *lactobacillus* is carried out by a TaqMan assay, the primer set of the region 1 primer as a forward primer and the region 2 primer as a reverse primer and the region 3 probe and/or the region 4 probe can be used. If either the intercalator-based real-time PCR assay or the TaqMan assay is used, the number of oral *lactobacillus* can be measured accurately. The TaqMan assay is preferable. In the TaqMan assay, a desired region of 16S ribosomal RNA gene of *Lactobacillus* is specifically amplified for measurement, because a specific probe is used in addition to at least two specific primers. Thus, the number of oral *lactobacillus* can be measured more accurately.

Conventionally performed PCR methods may be used in the present invention. In the PCR method, more specifically, a DNA synthesis reaction consisting of following three steps are repeated.
(1) First, a double-stranded DNA as a template is heated and denatured to become a single-stranded DNA.
(2) Next, two primers form a double strand DNA structure with a complementary region of the single stranded DNA respectively by cooling a reaction mixture containing the excess primers complementary to each end of a desired DNA region to be amplified.
(3) In the above condition, if deoxyribonucleotide triphosphate as a substrate and Taq DNA polymerase are added to the reaction mixture, complementary DNA are synthesized from the primers by the Taq DNA polymerase.

In the case of an intercalator-based real-time PCR assay, an intercalator such as SYBR Green I and the like is added to the reaction mixture, and then a fluorescence of intercalator bound to the synthesized double stranded DNA is measured per cycle. In the case of the TaqMan assay, the TaqMan probe is added to a reaction mixture, and then fluorescence generated from a reporter dye detached from the degraded TaqMan probe is measured each cycle.

As mentioned above, in the TaqMan method, a labeled probe, wherein a reporter dye is bound to one terminus such as a 5'-terminus of an oligonucleotide and a quencher dye is bound to the other terminus such as a 3'-terminus thereof, may be used. The reporter dye is a compound capable of generating fluorescence by a radiation of excitation light. If the reporter dye and quencher dye are bound together to one oligonucleotide, an energy absorbed by the reporter dye is absorbed into the quencher dye by an energy-transfer due to a close distance therebetween. Therefore, the reporter dye cannot be excited, and thus a natural fluorescence cannot be generated. This phenomenon is referred to as an optical quenching of fluorescence i.e. quenching. When the quenched probe is added to a reaction mixture, the probe hybridizes with a single strand DNA as a template in an annealing step. Subsequently, a Taq DNA polymerase synthesizes a new complementary DNA from a 3'-terminus of a primer and degrades the hybridized probe during synthesizing. Then, as a nick-translation occurs, the adjoining reporter dye and quencher dye are segregated, and thus the reporter dye previously subjected to an inhibition by quenching can generate a fluorescence. The above reaction occurs once per one molecule in a cycle of the PCR assay, and thus, an increase of a fluorescence intensity of the reporter dye almost correlates to the PCR reaction i.e. the amount of PCR products. According to the measuring method using the reporter dye and quencher dye, the measurement can be carried out without separating reaction products after the PCR assay, that is, can be carried out in real time.

As a sample to be used in the present invention, saliva, bacterial plaque or the like collected from an oral cavity may be used. The saliva or the bacterial plaque can be adjusted to an appropriate viscosity for measurement, if necessary. For example, after a subject to be tested has bitten paraffin wax, the saliva may be collected from the subject. Further, for example, the bacterial plaque may be collected from the subject by means of an exploratory needle or a pick.

In particular, the method for measuring the number of oral *lactobacillus* of the present invention comprises the following steps;
(1) extracting DNA from samples to be tested,
(2) amplifying the extracted DNA as a template by means of the primer set or the primers-probe set, and
(3) detecting the amplified DNA.

The extraction of DNA contained in saliva or bacterial plaque collected from the oral cavity in the step 1, can be carried out by means of commercially available DNA extraction kit in accordance with an attached protocol. Alternatively, the saliva, bacterial plaque or the like is suspended in a buffer or a solution containing detergent and the like for bacteriolysis, and the suspension is heated at 80° C. to 100° C., for 1 to 30 minutes to lyse *lactobacillus*. The whole suspension or a supernatant after centrifuging the whole suspension can be used as the DNA sample.

In step (2) (the DNA amplifying step), the TaqMan assay example, comprises the following reactions:
(a) If *lactobacillus* are present in a sample, an exponential DNA amplification occurs using a DNA of *lactobacillus* as a template DNA.
(b) During amplification, a TaqMan probe hybridizes to a template DNA. When a complementary DNA is synthesized using the template DNA hybridized with a primer, the TaqMan probe is degraded by Taq DNA polymerase with an exonuclease activity.
(c) Therefore, a reporter dye and a quencher dye, which are bound to the TaqMan probe, are segregated, whereby the reporter dye becomes detectable. In other words, if *lactobacillus* exists in the sample, the reporter dye generates a fluorescence and can be detected.
(d) The fluorescence intensity is dependent on the number of cycles of the PCR, and thus is increased exponentially.
(e) Several standard samples containing bacteria of a predetermined concentration are prepared, and a threshold cycle value (hereinafter referred to as Ct value) of each standard sample, at which fluorescence intensity is quickly increased, is determined. Then, a linear standard curve is obtained by plotting the Ct value on a longitudinal axis and a log of the predetermined concentration of standard samples on an abscissa axis.
(f) A Ct value of an unknown sample in a concentration of bacteria is examined. Then the resulting Ct value is applied to the above standard curve whereby the bacteria concentration of the unknown sample is obtained.

In step (3) (the detecting step of amplified DNA), the fluorescence intensity is measured per PCR cycle, whereby an increase of PCR products can be measured in real time.

A kit of the present invention can be used in the method for measuring the number of oral *lactobacillus*, and is characterized by comprising at least the forward primer and reverse primer. Preferably, the kit should comprise the primer set consisting of the region 1 primer and the region 2 primer, and the region 3 probe and/or the region 4 probe.

The kit of the present invention may contain the forward primer, reverse primer and probe, as a separate compound respectively, or as a mixture thereof. The kit of the present invention may also contain a desired reagent, and/or an enzyme for real-time PCR in addition to the primers and the probe.

Function

The primers-probe set of the present invention, and some primers-probe sets used in after-mentioned comparative examples 1 to 3 are designed from regions selected from base sequence regions with high homology in the 16S ribosomal RNA gene of *Lactobacillus rhamnosus, Lactobacillus casei, Lactobacillus salivarius, Lactobacillus gasseri, Lactobacillus acidophilus, Lactobacillus crispatus*, and *Lactobacillus fermentum*. Among these primers-probe set, according to the real-time PCR assay using the primers-probe set of the present invention, the obtained measurement value can be correlated with the number of *lactobacillus* obtained by the culture method. However, for the real-time PCR assay by the primers-probe set used in comparative examples 1 to 3, the obtained measurement value cannot be correlated with that obtained by the culture method. The reason for this has not been fully elucidated, but is presumed to be as follows (the present invention is by no means limited to the following explanation).

A region of the base sequence for the primers-probe set of the present invention should be selected from a base sequence of a kind of certain *lactobacillus*, but also from a common base sequence of all oral *lactobacillus*. However, the common base sequence is sometimes identical with a base sequence of indigenous bacteria in an oral cavity, and thus it is considered that a gene of indigenous bacteria in an oral cavity other than oral *lactobacillus* is often detected by the primers and probe of the selected region.

Further, the quality of primer(s) would be influenced by a region, base sequence, length and combination thereof. In the primer set of the present invention, it is particularly important that the number of oral *lactobacillus* obtained by real-time PCR using the primer set is well correlated with that obtained by the culture method. To accomplish the object, selection of regions of primers, and combination of a forward primer and a reverse primer is important. The object is accomplished, for example by use of primer set of the region 1 primer and the region 2 primer. Conversely, in the real-time PCR method using primer and probe set prepared in Comparative Examples 1 to 3, obtained number of oral *lactobacillus* is not correlated with the number of oral *lactobacillus* obtained by the culture method demonstrating that it is important to select appropriate region for primer. Further, in Comparative Example 2, R5 primer i.e. region 2 primer was used, but desired results were not obtained. This is because a combination of R5 primer and a forward primer other than region 1 primer was used, indicating that it is important to select an appropriate combination of primers.

There are three possible explanations for this: First, the primer binding region of a desired DNA easily forms a secondary structure such as a hairpin loop when the desired DNA is denatured to become a single stranded DNA. In such cases, the binding of primers and probe to the desired DNA is inhibited. Second, a primer dimer is formed by a binding between primers. Third, it is considered that the primer or probe per se form a secondary structure such as a hairpin loop. Accordingly, to accurately measure the number of oral *lactobacillus*, the regions with a common base sequence of all oral *lactobacillus* are selected, and of those regions, a region suitable for a real-time PCR assay and usable to obtain an accurate measurement should be selected.

EXAMPLES

The present invention now will be further illustrated by, but is by no means limited to, the following Examples.

Extraction of DNA 0.2 mL of Saliva was collected from the oral cavity of five subjects to be tested, and was then suspended in 1.6 mL of sterilized water, to adjust the viscosity, and the whole was centrifuged to obtain a pellet. From the pellet, 0.2 mL of DNA sample was extracted using a DNA extraction kit (QuickGene DNA tissue kit S; FUJIFILM Corporation) in accordance with a manual attached to the kit.

Example 1

The number of *lactobacillus* was measured by TaqMan assay using the region 1 primer, region 2 primer and region 3 probe. The resulting DNA sample and the following amounts of reagents were mixed in a tube, to prepare a total volume of 20 μL of a reaction mixture.

| | |
|---|---|
| TaqMan Fast Universal PCR Mater Mix | 10 μL |
| 10 μM of F9 forward primer | 0.4 μL (final concentration of 200 nM) |
| 10 μM of R3 reverse primer | 0.4 μL (final concentration of 200 nM) |
| 5 μM of P4 probe | 0.4 μL (final concentration of 100 nM) |
| DNA sample | 1.0 μL |
| sterilized water | 7.8 μL |

The tubes containing 20 μL of the reaction mixture were placed in an Applied Biosystems 7500 Fast real-time PCR system, and then a PCR reaction was carried out. After an incubation at 95° C. for 20 seconds was carried out as a pretreatment, a cycle composed of treatments at 95° C. for 3 seconds, and at 60° C. for 30 seconds, was repeated 45 times. A fluorescence intensity was measured per each cycle. Chemical synthesized oligonucleotides were used as primers, and a chemical synthesized oligonucleotide, in which FAM is bound to a 5'-terminus thereof and TAMRA is bound to a 3'-terminus thereof, was used as a probe.

In order to prepare a standard curve, a *Lactobacillus rhamnosus* JCM 1136 strain was cultured and diluted to prepare various concentrations of standard bacterial samples. A threshold cycle (Ct value) of each standard bacterial sample, at which fluorescence intensity is quickly increased, was examined, and then a standard curve wherein a longitudinal axis is Ct value, and an abscissa axis is a log of the concentration of standard bacterial samples is prepared. Simultaneously, Ct values of the samples were also examined and the bacterial concentration of the samples was estimated from a standard curve. The results are shown in Table 4.

Example 2

The number of *lactobacillus* was measured by TaqMan assay using the region 1 primer, region 2 primer and region 3 probe, which were different from primers and probe used in Example 1.

That is, the procedure described in Example 1 was repeated except that an F6 forward primer as a forward primer, an R1 reverse primer as a reverse primer, and a P3 probe as a probe were used. The results are shown in Table 4.

Comparative Example 1

The number of lactobacillus was measured by TaqMan assay using a combination of primers and probe, which were different from the combination of the region 1 primer, region 2 primer and region 3 probe.

The procedure described in Example 1 was repeated except that an F11 forward primer (SEQ ID NO:39) as a forward primer, an R4 reverse primer (SEQ ID NO:40) as a reverse primer, and a P11 probe (SEQ ID NO:41) as a probe were used. Each primer was designed on the basis of a base sequence region with high homology in a 16S ribosomal RNA gene of *Lactobacillus rhamnosus, Lactobacillus casei, Lactobacillus salivarius, Lactobacillus gasseri, Lactobacillus acidophilus, Lactobacillus crispatus*, and *Lactobacillus fermentum*. In particular, F11 forward primer and P11 probe were designed from a base sequence region identical among above all *lactobacillus*. The base sequence of the F11 forward primer, R4 reverse primer, and P11 probe are shown as follows. The corresponding nucleotide numbers in a base sequence of *Lactobacillus rhamnosus* of SEQ ID NO:47 are shown in parentheses.

```
F11:   5'-GCAGCAGTAGGGAATCTTCCA-3'      (369-389)

R4:    5'-TTAAGCCGAGGGCTTTCACA-3'       (621-640)

P11:   5'-CGTGCCAGCAGCCGCGGTAATAC-3'    (532-554)
```

The results are shown in Table 4.

Comparative Example 2

The number of lactobacillus was measured by TaqMan assay using a combination of primers and probe, which were different from the combination of the region 1 primer, region 2 primer and region 3 probe.

The procedure described in Example 1 was repeated except that an F12 forward primer (SEQ ID NO: 42) as a forward primer, an R5 reverse primer (SEQ ID NO: 43) as a reverse primer, and a P12 probe (SEQ ID NO: 44) as a probe were used. Each primer was designed on the basis of a base sequence region with high homology in a 16S ribosomal RNA gene of *Lactobacillus rhamnosus, Lactobacillus casei, Lactobacillus salivarius, Lactobacillus gasseri, Lactobacillus acidophilus, Lactobacillus crispatus*, and *Lactobacillus fermentum*. In particular, F12 forward primer and R5 reverse primer were designed from a base sequence region identical among above all *Lactobacillus* species. R5 reverse primer corresponds to the region 2 primer. The base sequence of the F12 forward primer, R5 reverse primer, and P12 probe are shown as follows. The corresponding nucleotide numbers in a base sequence of *Lactobacillus rhamnosus* of SEQ ID NO:47 are shown in parentheses.

```
F12:
5'-ATGGAAGAACACCAGTGGCG-3'              (726-745)

R5:
5'-GCGGTCGTACTCCCCAGG-3'                (901-918)

P12:
5'-CCGTAAACGATGAATGCTAGGTGTTGGAGG-3'    (828-857)
```

The results are shown in Table 4.

Comparative Example 3

The number of *Lactobacillus* was measured by an intercalator-based real-time PCR assay i.e. SYBR Green method using primers described in non-patent reference No. 4. The resulting DNA sample and the following amounts of reagents were mixed in a tube, to prepare a total volume of 20 μL of a reaction mixture, in accordance with a manual attached to the SYBR Green PCR Mater Mix (Applied Biosystems Japan Ltd.)

| | |
|---|---|
| SYBR Green PCR Mater Mix | 10 μL |
| 10 μM of Lacto forward primer | 0.2 μL (final concentration of 100 nM) |
| 10 μM of Lacto reverse primer | 0.2 μL (final concentration of 100 nM) |
| DNA sample | 1.0 μL |
| sterilized water | 8.6 μL |

The base sequence of the Lacto F primer (SEQ ID NO:45), Lacto R primer (SEQ ID NO:46) are shown as follows.

```
Lacto F:  5'-TGGAAACAGRTGCTAATACCG-3'

Lacto R:  5'-GTCCATTGTGGAAGATTCCC-3'
```

The tubes containing 20 μL of the reaction mixture were placed in an Applied Biosystems 7500 Fast real-time PCR system, and then a PCR reaction was carried out. After an incubation at 50° C. for 2 minutes and 95° C. for 10 minutes was carried out as a pretreatment, a cycle composed of treatments at 95° C. for 15 seconds, and at 62° C. for 1 minutes, was repeated 45 times. A fluorescence intensity was measured for per cycle. Chemical synthesized oligonucleotides were used as primers.

In order to prepare a standard curve, a *Lactobacillus rhamnosus* JCM 1136 strain was cultured and diluted to prepare various concentrations of standard bacterial samples. A threshold cycle (Ct value) of each standard bacterial sample, at which fluorescence intensity is quickly increased, was examined, and then a standard curve wherein a longitudinal axis is Ct value, and an abscissa axis is a log of the concentration of standard bacterial samples is prepared. Simultaneously, Ct values of the samples were also examined and the bacterial concentration of the samples was estimated from a standard curve. The results are shown in Table 4.

The measurement values by real-time PCR assay in Examples 1 to 2 and Comparative Examples 1 to 3 are calculated from the standard curve, and unit of the measurement value is cell/mL.

The saliva collected from the oral cavity of the subjects was diluted to an appropriate concentration, and inoculated on a ROGOSA agar medium plate. The numbers of oral *lactobacillus* were measured by counting numbers of a colony. The results are shown in Table 4.

TABLE 4

|  | Example 1 | Example 2 | Comparative Example 1 | Comparative Example 2 | Comparative Example 3 | Culture 1) method |
|---|---|---|---|---|---|---|
| Forward Primer | F9 | F6 | F11 | F12 | LactoF |  |
| Reverse Primer | R3 | R1 | R4 | R5 | LactoR |  |
| Probe | P4 | P3 | P11 | P12 | unmesurable |  |
| Subject A | $8.5 \times 10^5$ | $7.5 \times 10^5$ | $3.5 \times 10^7$ | $6.1 \times 10^7$ | $2.0 \times 10^3$ | $6.0 \times 10^5$ |
| Subject B | $1.3 \times 10^4$ | $5.8 \times 10^3$ | $1.6 \times 10^8$ | $7.2 \times 10^6$ | $5.9 \times 10^4$ | $8.9 \times 10^3$ |
| Subject C | unmesurable | unmesurable | $2.0 \times 10^8$ | $4.6 \times 10^7$ | $1.0 \times 10^4$ | unmesurable |
| Subject D | $4.0 \times 10^3$ | $5.5 \times 10^3$ | $7.0 \times 10^7$ | $9.6 \times 10^6$ | $3.7 \times 10^5$ | $3.1 \times 10^3$ |
| Subject E | $2.8 \times 10^4$ | $4.6 \times 10^4$ | $2.3 \times 10^8$ | $5.5 \times 10^7$ | $7.0 \times 10^5$ | $3.6 \times 10^4$ |

1) unit: CFU/mL

As shown in Table 4, according to the real-time PCR assay using the primers-probe set of the present invention, the number of oral *lactobacillus* can be measured accurately in a short time. Further, the measurement value can be correlated with the number of *lactobacillus* obtained by the culture method. Therefore, the number of oral *lactobacillus* present in an oral cavity can be measured effectively by use of the method and kit of the present invention. On the contrary, when the primers and probes described Comparative Examples 1 and 2 are used, the number of oral *lactobacillus* cannot be correlated with those obtained by the culture method, and therefore, the number of oral *lactobacillus* could not be accurately measured. In addition, when the primers described Comparative Examples 3 are used, the number of oral *lactobacillus* cannot be correlated with that obtained by the culture method.

INDUSTRIAL APPLICABILITY

Utilizing the method for measuring the number of oral *lactobacillus* using the primers-probe set of the present invention, the number of *lactobacillus* can be measured. The measurement of the number of *lactobacillus* is usable for a detection of the risk of development of dental caries and useful for a prevention and treatment of dental caries. Additionally, using the present invention, many samples can be measured, compared with the culture method, and thus the measurement can be carried out effectively in a medical laboratory and so on.

The invention claimed is:

1. A primer set for measuring the number of oral *lactobacillus*, comprising at least one forward primer selected from the group consisting of oligonucleotides of the base sequence of SEQ ID NO: 16, SEQ ID NO: 17, SEQ ID NO: 18, SEQ ID NO: 19, SEQ ID NO: 20, SEQ ID NO: 21, SEQ ID NO: 22, SEO ID NO: 23, SEQ ID NO: 24, and SEQ ID NO: 25, and at least one reverse primer selected from the group consisting of oligonucleotides of the base sequence of SEQ ID NO: 26, SEQ ID NO: 27, and SEQ ID NO: 28.

2. A primers-probe set comprising the primer set according to claim 1, and at least one probe comprising an oligonucleotide part of at least 10 sequential bases in a base sequence of 5'-GGTTTCCGCCYYTCAGTGCYGSAGCTAACGCA-3' (wherein Y is T or C, and S is G or C; SEQ ID NO:8), 5'-GGTTTCCGCCCTTCAGTGCCGCAGCTAACGCA-3' (SEQ ID NO:9), 5'-GGTTTCCGCCTCTCAGTGCTGCAGCTAACGCA-3'(SEQ ID NO:10), 5'-GGTTTCCGCCCTTCAGTGCCGGAGCTAACGCA-3'(SEQ ID NO:11), 5'-TGCGTTAGCTSCRGCACTGARRGGCGGAAACC-3' (wherein R is G or A, and S is G or C;SEQ ID NO:12), 5'-TGCGTTAGCTGCGGCACTGAAGGGCGGAAACC-3' (SEQ ID NO:13), 5'-TGCGTTAGCTGCAGCACTGAGAGGCGGAAACC-3'(SEQ ID NO:14), or 5'-TGCGTTAGCTCCGGCACTGAAGGGCGGAAACC-3'(SEQ ID NO:15).

3. The primers-probe set according to claim 2, wherein the probe is an oligonucleotide of the base sequence of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, or a mixture of two or more of the oligonucleotides.

4. A method for measuring the number of oral *lactobacillus* by a real-time PCR assay using the primer set according to claim 1.

5. A method for measuring the number of oral *lactobacillus* by a real-time PCR assay using the primers-probe set according to claim 2.

6. A real-time PCR kit for measuring the number of oral *lactobacillus*, comprising the primer set according to claim 1 and instructions for interpreting results.

7. A real-time PCR kit for measuring the number of oral *lactobacillus*, comprising the primers-probe set according to claim 2 and instructions.

* * * * *

SEQUENCE LISTING

<160> NUMBER OF SEQ ID NOS: 47

<210> SEQ ID NO 1
<211> LENGTH: 36
<212> TYPE: DNA
<213> ORGANISM: Artificial
<220> FEATURE:
<221> NAME/KEY: misc_feature
<222> LOCATION: 1..36
<223> OTHER INFORMATION: primer
<220> FEATURE:
<221> NAME/KEY: misc_difference
<222> LOCATION: 15..15
<223> OTHER INFORMATION: r is g or a
<220> FEATURE:
<221> NAME/KEY: misc_difference
<222> LOCATION: 21..21
<223> OTHER INFORMATION: r is g or a
<220> FEATURE:
<221> NAME/KEY: misc_difference
<222> LOCATION: 29..30
<223> OTHER INFORMATION: r is g or a

<400> SEQUENCE: 1
gccgtaaacg atgartgcta rgtgttggrr ggtttc        36

<210> SEQ ID NO 2
<211> LENGTH: 36
<212> TYPE: DNA
<213> ORGANISM: Lactobacillus salivarius

<400> SEQUENCE: 2
gccgtaaacg atgaatgcta ggtgttggag ggtttc        36

<210> SEQ ID NO 3
<211> LENGTH: 36

```
<212> TYPE: DNA
<213> ORGANISM: Lactobacillus acidophilus

<400> SEQUENCE: 3
gccgtaaacg atgagtgcta agtgttggga ggtttc                              36

<210> SEQ ID NO 4
<211> LENGTH: 36
<212> TYPE: DNA
<213> ORGANISM: Lactobacillus fermentum

<400> SEQUENCE: 4
gccgtaaacg atgagtgcta ggtgttggag ggtttc                              36

<210> SEQ ID NO 5
<211> LENGTH: 30
<212> TYPE: DNA
<213> ORGANISM: Artificial
<220> FEATURE:
<221> NAME/KEY: misc_feature
<222> LOCATION: 1..30
<223> OTHER INFORMATION: primer
<220> FEATURE:
<221> NAME/KEY: misc_difference
<222> LOCATION: 24..24
<223> OTHER INFORMATION: r is g or a

<400> SEQUENCE: 5
tgcggtcgta ctccccaggc ggartgctta                                     30

<210> SEQ ID NO 6
<211> LENGTH: 30
<212> TYPE: DNA
<213> ORGANISM: Lactobacillus salivarius

<400> SEQUENCE: 6
tgcggtcgta ctccccaggc ggaatgctta                                     30

<210> SEQ ID NO 7
<211> LENGTH: 30
<212> TYPE: DNA
<213> ORGANISM: Lactobacillus acidophilus

<400> SEQUENCE: 7
tgcggtcgta ctccccaggc ggagtgctta                                     30

<210> SEQ ID NO 8
<211> LENGTH: 32
<212> TYPE: DNA
<213> ORGANISM: Artificial
<220> FEATURE:
<221> NAME/KEY: misc_feature
<222> LOCATION: 1..32
<223> OTHER INFORMATION: primer
<220> FEATURE:
<221> NAME/KEY: misc_difference
<222> LOCATION: 11..12
<223> OTHER INFORMATION: y is t or c
<220> FEATURE:
<221> NAME/KEY: misc_difference
<222> LOCATION: 20..20
<223> OTHER INFORMATION: y is t or c
<220> FEATURE:
<221> NAME/KEY: misc_difference
<222> LOCATION: 22..22
<223> OTHER INFORMATION: s is g or c

<400> SEQUENCE: 8
ggtttccgcc yytcagtgcy gsagctaacg ca                                  32
```

<210> SEQ ID NO 9
<211> LENGTH: 32
<212> TYPE: DNA
<213> ORGANISM: Lactobacillus salivarius

<400> SEQUENCE: 9
ggtttccgcc cttcagtgcc gcagctaacg ca                          32

<210> SEQ ID NO 10
<211> LENGTH: 32
<212> TYPE: DNA
<213> ORGANISM: Lactobacillus acidophilus

<400> SEQUENCE: 10
ggtttccgcc tctcagtgct gcagctaacg ca                          32

<210> SEQ ID NO 11
<211> LENGTH: 32
<212> TYPE: DNA
<213> ORGANISM: Lactobacillus fermentum

<400> SEQUENCE: 11
ggtttccgcc cttcagtgcc ggagctaacg ca                          32

<210> SEQ ID NO 12
<211> LENGTH: 32
<212> TYPE: DNA
<213> ORGANISM: Artificial
<220> FEATURE:
<221> NAME/KEY: misc_feature
<222> LOCATION: 1..32
<223> OTHER INFORMATION: primer
<220> FEATURE:
<221> NAME/KEY: misc_difference
<222> LOCATION: 11..11
<223> OTHER INFORMATION: s is g or c
<220> FEATURE:
<221> NAME/KEY: misc_difference
<222> LOCATION: 13..13
<223> OTHER INFORMATION: r is g or a
<220> FEATURE:
<221> NAME/KEY: misc_difference
<222> LOCATION: 21..22
<223> OTHER INFORMATION: r is g or a

<400> SEQUENCE: 12
tgcgttagct scrgcactga rrggcggaaa cc                          32

<210> SEQ ID NO 13
<211> LENGTH: 32
<212> TYPE: DNA
<213> ORGANISM: Lactobacillus salivarius

<400> SEQUENCE: 13
tgcgttagct gcggcactga agggcggaaa cc                          32

<210> SEQ ID NO 14
<211> LENGTH: 32
<212> TYPE: DNA
<213> ORGANISM: Lactobacillus acidophilus

<400> SEQUENCE: 14
tgcgttagct gcagcactga gaggcggaaa cc                          32

<210> SEQ ID NO 15
<211> LENGTH: 32

<212> TYPE: DNA
<213> ORGANISM: Lactobacillus fermentum

<400> SEQUENCE: 15
tgcgttagct ccggcactga agggcggaaa cc        32

<210> SEQ ID NO 16
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: primer

<400> SEQUENCE: 16
acgatgaatg ctaggtgttg gag        23

<210> SEQ ID NO 17
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: primer

<400> SEQUENCE: 17
acgatgaatg ctaggtgttg ga        22

<210> SEQ ID NO 18
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: primer

<400> SEQUENCE: 18
cgatgaatgc taggtgttgg ag        22

<210> SEQ ID NO 19
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: primer

<400> SEQUENCE: 19
atgaatgcta ggtgttggag ggt        23

<210> SEQ ID NO 20
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: primer

<400> SEQUENCE: 20
atgaatgcta ggtgttggag gg        22

<210> SEQ ID NO 21
<211> LENGTH: 22

```
<212> TYPE: DNA
<213> ORGANISM: Artificial
<220> FEATURE:
<221> NAME/KEY: misc_feature
<222> LOCATION: 1..22
<223> OTHER INFORMATION: primer

<400> SEQUENCE: 21
tgaatgctag gtgttggagg gt                                              22

<210> SEQ ID NO 22
<211> LENGTH: 21
<212> TYPE: DNA
<213> ORGANISM: Artificial
<220> FEATURE:
<221> NAME/KEY: misc_feature
<222> LOCATION: 1..21
<223> OTHER INFORMATION: primer

<400> SEQUENCE: 22
tgaatgctag gtgttggagg g                                               21

<210> SEQ ID NO 23
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: primer

<400> SEQUENCE: 23
gaatgctagg tgttggaggg ttt                                             23

<210> SEQ ID NO 24
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: primer

<400> SEQUENCE: 24
aatgctaggt gttggagggt ttc                                             23

<210> SEQ ID NO 25
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: primer

<400> SEQUENCE: 25
atgctaggtg ttggagggtt tc                                              22

<210> SEQ ID NO 26
<211> LENGTH: 18
<212> TYPE: DNA
<213> ORGANISM: Artificial
<220> FEATURE:
<221> NAME/KEY: misc_feature
<222> LOCATION: 1..18
<223> OTHER INFORMATION: primer

<400> SEQUENCE: 26
tactccccag gcggaatg                                                   18
```

```
<210> SEQ ID NO 27
<211> LENGTH: 17
<212> TYPE: DNA
<213> ORGANISM: Artificial
<220> FEATURE:
<221> NAME/KEY: misc_feature
<222> LOCATION: 1..17
<223> OTHER INFORMATION: primer

<400> SEQUENCE: 27
actccccagg cggaatg                                                      17

<210> SEQ ID NO 28
<211> LENGTH: 16
<212> TYPE: DNA
<213> ORGANISM: Artificial
<220> FEATURE:
<221> NAME/KEY: misc_feature
<222> LOCATION: 1..16
<223> OTHER INFORMATION: primer

<400> SEQUENCE: 28
ccccaggcgg aatgct                                                       16

<210> SEQ ID NO 29
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe

<400> SEQUENCE: 29
cgcccttcag tgccgcagct aac                                               23

<210> SEQ ID NO 30
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: probe

<400> SEQUENCE: 30
cgcccttcag tgccgcagct aa                                                22

<210> SEQ ID NO 31
<211> LENGTH: 21
<212> TYPE: DNA
<213> ORGANISM: Artificial
<220> FEATURE:
<221> NAME/KEY: misc_feature
<222> LOCATION: 1..21
<223> OTHER INFORMATION: probe

<400> SEQUENCE: 31
cgcccttcag tgccgcagct a                                                 21

<210> SEQ ID NO 32
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe
```

```
<400> SEQUENCE: 32
cccttcagtg ccgcagctaa cgc                                              23

<210> SEQ ID NO 33
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe

<400> SEQUENCE: 33
ccttcagtgc cgcagctaac gca                                              23

<210> SEQ ID NO 34
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe

<400> SEQUENCE: 34
gttagctgcg gcactgaagg gcg                                              23

<210> SEQ ID NO 35
<211> LENGTH: 22
<212> TYPE: DNA
<213> ORGANISM: Artificial
<220> FEATURE:
<221> NAME/KEY: misc_feature
<222> LOCATION: 1..22
<223> OTHER INFORMATION: probe

<400> SEQUENCE: 35
ttagctgcgg cactgaaggg cg                                               22

<210> SEQ ID NO 36
<211> LENGTH: 21
<212> TYPE: DNA
<213> ORGANISM: Artificial
<220> FEATURE:
<221> NAME/KEY: misc_feature
<222> LOCATION: 1..21
<223> OTHER INFORMATION: probe

<400> SEQUENCE: 36
tagctgcggc actgaagggc g                                                21

<210> SEQ ID NO 37
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe

<400> SEQUENCE: 37
gcgttagctg cggcactgaa ggg                                              23

<210> SEQ ID NO 38
<211> LENGTH: 23
<212> TYPE: DNA
<213> ORGANISM: Artificial
```

```
<220> FEATURE:
<221> NAME/KEY: misc_feature
<222> LOCATION: 1..23
<223> OTHER INFORMATION: probe

<400> SEQUENCE: 38
tgcgttagct gcggcactga agg                                              23

<210> SEQ ID NO 39
<211> LENGTH: 21
<212> TYPE: DNA
<213> ORGANISM: Artificial
<220> FEATURE:
<221> NAME/KEY: misc_feature
<222> LOCATION: 1..21
<223> OTHER INFORMATION: probe

<400> SEQUENCE: 39
gcagcagtag ggaatcttcc a                                                21

<210> SEQ ID NO 40
<211> LENGTH: 20
<212> TYPE: DNA
<213> ORGANISM: Artificial
<220> FEATURE:
<221> NAME/KEY: misc_feature
<222> LOCATION: 1..20
<223> OTHER INFORMATION: primer

<400> SEQUENCE: 40
ttaagccgag ggctttcaca                                                  20

<210> SEQ ID NO 41
<211> LENGTH: 23
<212> TYPE: DNA
<213> ORGANISM: Artificial
<220> FEATURE:
<221> NAME/KEY: misc_feature
<222> LOCATION: 1..23
<223> OTHER INFORMATION: probe

<400> SEQUENCE: 41
cgtgccagca gccgcggtaa tac                                              23

<210> SEQ ID NO 42
<211> LENGTH: 20
<212> TYPE: DNA
<213> ORGANISM: Artificial
<220> FEATURE:
<221> NAME/KEY: misc_feature
<222> LOCATION: 1..20
<223> OTHER INFORMATION: primer

<400> SEQUENCE: 42
atggaagaac accagtggcg                                                  20

<210> SEQ ID NO 43
<211> LENGTH: 18
<212> TYPE: DNA
<213> ORGANISM: Artificial
<220> FEATURE:
<221> NAME/KEY: misc_feature
<222> LOCATION: 1..18
<223> OTHER INFORMATION: primer

<400> SEQUENCE: 43
gcggtcgtac tccccagg                                                    18
```

```
<210> SEQ ID NO 44
<211> LENGTH: 30
<212> TYPE: DNA
<213> ORGANISM: Artificial
<220> FEATURE:
<221> NAME/KEY: misc_feature
<222> LOCATION: 1..30
<223> OTHER INFORMATION: probe

<400> SEQUENCE: 44
ccgtaaacga tgaatgctag gtgttggagg                                          30

<210> SEQ ID NO 45
<211> LENGTH: 20
<212> TYPE: DNA
<213> ORGANISM: Artificial
<220> FEATURE:
<221> NAME/KEY: misc_feature
<222> LOCATION: 1..20
<223> OTHER INFORMATION: primer

<400> SEQUENCE: 45
tggaaacagr tgctaatacc                                                     20

<210> SEQ ID NO 46
<211> LENGTH: 20
<212> TYPE: DNA
<213> ORGANISM: Artificial
<220> FEATURE:
<221> NAME/KEY: misc_feature
<222> LOCATION: 1..20
<223> OTHER INFORMATION: primer

<400> SEQUENCE: 46
gtccattgtg gaagattccc                                                     20

<210> SEQ ID NO 47
<211> LENGTH: 1562
<212> TYPE: DNA
<213> ORGANISM: Lactobacillus rhamnosus

<400> SEQUENCE: 47
agagtttgat cctggctcag gatgaacgct ggcggcgtgc ctaatacatg caagtcgaac         60
gagttctgat tattgaaagg tgcttgcatc ttgatttaat tttgaacgag tggcggacgg        120
gtgagtaaca cgtgggtaac ctgcccttaa gtggggata acatttggaa acagatgcta         180
ataccgcata atccaagaa ccgcatggtt cttggctgaa agatggcgta agctatcgct         240
tttggatgga cccgcggcgt attagctagt tggtgaggta acggctcacc aaggcaatga        300
tacgtagccg aactgagagg ttgatcggcc acattgggac tgagacacgg cccaaactcc        360
tacgggaggc agcagtaggg aatcttccac aatggacgca agtctgatgg agcaacgccg        420
cgtgagtgaa gaaggctttc gggtcgtaaa actctgttgt tggagaagaa tggtcggcag        480
agtaactgtt gtcggcgtga cggtatccaa ccagaaagcc acggctaact acgtgccagc        540
agccgcggta atacgtaggt ggcaagcgtt atccggattt attgggcgta aagcgagcgc        600
aggcggtttt ttaagtctga tgtgaaagcc ctcggcttaa ccgaggaagt gcatcggaaa        660
ctggaaaact tgagtgcaga gaggacagt ggaactccat gtgtagcggt gaaatgcgta         720
gatatatgga agaacaccag tggcgaaggc ggctgtctgg tctgtaactg acgctgaggc        780
tcgaaagcat gggtagcgaa caggattaga taccctggta gtccatgccg taaacgatga       840
atgctaggtg ttgaggggtt tccgcccttc agtgccgcag ctaacgcatt aagcattccg       900
cctggggagt acgaccgcaa ggttgaaact caaaggaatt gacgggggcc cgcacaagcg       960
```

-continued

```
gtggagcatg tggtttaatt cgaagcaacg cgaagaacct taccaggtct tgacatcttt    1020
tgatcacctg agagatcggg tttccccttc gggggcaaaa tgacaggtgg tgcatggttg    1080
tcgtcagctc gtgtcgtgag atgttgggtt aagtcccgca acgagcgcaa cccttatgac    1140
tagttgccag catttagttg ggcactctag taagactgcc ggtgacaaac cggaggaagg    1200
tggggatggc gtcaaatcat catgcccctt atgacctggg ctacacacgt gctacaatgg    1260
atggtacaac gagttgcgag accgcgaggc caagctaatc tcttaaagcc attctcagtt    1320
cggactgtag gctgcaactc gcctacacga agtcggaatc gctagtaatc gcggatcagc    1380
acgccgcggt gaatacgttc ccgggccttg tacacaccgc ccgtcacacc atgagagttt    1440
gtaacacccg aagccggtgg cgtaaccctt ttagggagcg agccgtctaa ggtgggacaa    1500
atgattaggg tgaagtcgta acaaggtagc cgtaggagaa cctgcggctg gatcacctcc    1560
tt                                                                   1562
```